United States Patent
Urbanczyk et al.

(10) Patent No.: US 11,061,011 B2
(45) Date of Patent: Jul. 13, 2021

(54) METHOD FOR DETERMINING A TIME WINDOW IN WHICH A CASING PRESSURE TEST CAN BE PERFORMED WITHOUT DAMAGING A CEMENT SHEATH

(71) Applicant: TOTAL SE, Courbevoie (FR)

(72) Inventors: Christophe Urbanczyk, Pau (FR); André Garnier, Montardon (FR); Jean Sulem, Paris (FR); Siavash Ghabezloo, Bry sur Marne (FR); Nicolaine Agofack, Trondheim (NO)

(73) Assignee: TOTAL SE, Courbevoie (FR)

( * ) Notice: Subject to any disclaimer, the term of this patent is extended or adjusted under 35 U.S.C. 154(b) by 8 days.

(21) Appl. No.: 16/093,920

(22) PCT Filed: Apr. 15, 2016

(86) PCT No.: PCT/IB2016/000608
§ 371 (c)(1),
(2) Date: Oct. 15, 2018

(87) PCT Pub. No.: WO2017/178858
PCT Pub. Date: Oct. 19, 2017

(65) Prior Publication Data
US 2019/0086384 A1    Mar. 21, 2019

(51) Int. Cl.
*G01N 33/00*  (2006.01)
*G01N 33/38*  (2006.01)
*E21B 47/005* (2012.01)
*E21B 47/117* (2012.01)

(52) U.S. Cl.
CPC ......... *G01N 33/383* (2013.01); *E21B 47/005* (2020.05); *E21B 47/117* (2020.05)

(58) Field of Classification Search
CPC .............. G01N 33/383; E21B 47/0005; E21B 47/1025
USPC .......................................................... 73/803
See application file for complete search history.

(56) References Cited

U.S. PATENT DOCUMENTS

| | | |
|---|---|---|
| 5,554,855 A | 9/1996 | Ueno |
| 7,849,650 B2 | 12/2010 | Tonyan et al. |
| 8,794,078 B2 | 8/2014 | Darbe et al. |
| 9,803,523 B2 | 10/2017 | Hagg et al. |

(Continued)

FOREIGN PATENT DOCUMENTS

WO    WO 2015/143368 A1    9/2015

OTHER PUBLICATIONS

PCT International Search Report for PCT/IB2016/000608, dated Nov. 30, 2016, 2 pages.

(Continued)

*Primary Examiner* — Max H Noori
(74) *Attorney, Agent, or Firm* — Patterson Thuente Pedersen, P.A.

(57) ABSTRACT

The present invention relates to a method for determining a time window in which a casing pressure test can be performed without damaging a cement sheath. The time window is determined by: determining the hydration degree of the cement at a given time for a considered pressure and temperature values in the well; and then comparing the determined hydration degree to a predetermined value. If the determined hydration degree is below the predetermined value, then the casing pressure test can be done without damaging the cement.

7 Claims, 4 Drawing Sheets

(56) References Cited

U.S. PATENT DOCUMENTS

| | | | |
|---|---|---|---|
| 2002/0057095 A1 | 5/2002 | Zoughi et al. | |
| 2005/0138991 A1* | 6/2005 | Wallevik | B01F 7/063 |
| | | | 73/54.02 |
| 2005/0210995 A1 | 9/2005 | Drnevich et al. | |
| 2008/0178683 A1 | 7/2008 | Heathman et al. | |
| 2008/0233044 A1* | 9/2008 | Hansen | C04B 7/51 |
| | | | 423/640 |
| 2012/0158333 A1* | 6/2012 | Li | G01N 27/021 |
| | | | 702/65 |
| 2013/0192382 A1 | 8/2013 | Bois et al. | |
| 2014/0007695 A1 | 1/2014 | Darbe et al. | |
| 2015/0033862 A1* | 2/2015 | Bois | G01N 29/024 |
| | | | 73/597 |
| 2017/0183269 A1 | 6/2017 | Pearl, Jr. et al. | |
| 2018/0258337 A1 | 9/2018 | Contreras et al. | |

OTHER PUBLICATIONS

PCT Written Opinion of the ISA for PCT/IB2016/000608, dated Nov. 30, 2016, 6 pages.

Nicolaine Agofack: "Comportement des ciments pétroliers au jeune âge et intégrité des puits", , Jan. 1, 2016 (Jan. 1, 2016), XP055321461, Paris Retrieved from the Internet: URL:www.theses.fr/2015PESC1040/abes [retrieved on Nov. 21, 2016] abstract, 252 pages.

« Effets des contraintes et de la température sur l'intégrité des ciments des puits pétroliers », Manh Huyen VU, Feb. 23, 2012, 241 pages.

European Office Action from EP Application 16724106.6, dated Nov. 13, 2019, 4 pgs.

Office Action from GCC Application No. GC 2017-33208 dated Dec. 13, 2018, 4 pgs.

Application and File History for U.S. Appl. No. 16/093,887, filed Oct. 15, 2018, inventors Urbanczyk et al., as available in PAIR at www.uspto.gov.

Behrmann, L. A., Li, J. L., Venkitaraman, A. & Li, H., 1997. Borehole Dynamics During Underbalanced Perforating. Society of Petroleum Engineers, Issue SPE 38139, pp. 17-24.

Thiercelin, M. J., Dargaud, B., Baret, J. F. & Rodriguez, W. J., 1997. Cement Design Based on Cement Mechanical Response. Society of Petroleum Engineers, Issue SPE 38598, pp. 337-348.

American Petroleum Institute, "Isolating Potential Flow Zones During Well Construction", API Standard 65—Part 2, Second Edition, Dec. 2010, 96 pgs.

Thiercelin et al: "A Soil Mechanics Approach to Predict Cement Sheath Behavior", SPE/ISRM Rock Mechanics in Petroleum Engineering, Jul. 10, 1998 (Jul. 10, 1998), XP055292313, DOI: 10.2118/47375-MS.

Ghabezloo S. (2011) "*Micromechanics analysis of thermal expansion and thermal pressurization of a hardened cement paste* ", Cement and Concrete Research, 2011, 41(5), 520-532, DOI 10.1016/j.cemconres.2011.01.023.

\* cited by examiner

METHOD FOR DETERMINING A TIME WINDOW IN WHICH A CASING PRESSURE TEST CAN BE PERFORMED WITHOUT DAMAGING A CEMENT SHEATH

RELATED APPLICATIONS

The present application is a National Phase entry of PCT Application No. PCT/IB2016/00608, filed Apr. 15, 2016, said application being hereby incorporated by reference herein in its entirety.

FIELD OF THE INVENTION

The present invention relates to the domain of cement slurry hydration and especially during drilling operations.

BACKGROUND OF THE INVENTION

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section. Furthermore, all embodiments are not necessarily intended to solve all or even any of the problems brought forward in this section.

During the drilling of wells (e.g. hydrocarbon wells or oil wells or any kind of well in general), a mud with very specific physical properties is injected in the well to, for instance, support the walls of the drilled geological formations.

The hydrostatic pressure of the mud is, in most of the case, greater than the fluid pressure in the formation, but its equivalent circulating density should not exceed the fracture pressure of these geological formations.

A casing is then run into the well.

Cement slurries are pumped inside the casing and displaced in the annulus, so that it can fill the annular space between the casings and/or the geological formations.

The cement sheath allows protecting/preventing the casing against corrosion by isolating the casing from the geological formation fluids.

According to the API standards (API STD 65-2, 2010), the geological formations can be drilled when the cement sheath has developed a uniaxial compressive strength of around 50 psi API section 4.6.3, API section 5.7.9 (0.345 MPa).

Nevertheless, the setting of the cement is a function of a plurality of parameters: temperature, pressure, additives (accelerators, retarders, extenders, water/cement ratio, etc.).

For a given hydration degree, the cement evolves from a liquid to a solid with mechanical properties. It is noted that mechanical and thermal loadings may cause damage if the cement has not developed sufficient mechanical properties.

It is important to take into account the evolution of hydration degree for defining when the cement can be put a strain on without creating damage.

Theses loadings (mechanical and thermal) may be related to the "casing tests" or "casing pressure test", during which the oil/gas operators check the casing integrity.

During a casing pressure test, the applied pressure may vary from a few tens of megapascals (i.e. MPa) to more than 100 MPa. According Behrmann et al., 1997 and Thiercelin et al., 1997, the pressure in the wells during the drilling may exceed 40 MPa.

These thermal and or mechanical loadings can damage the cement. For example, it may result in:
 (a) debonding or separation between the cement sheath and the casing or between the cement sheath and geological formations, which can lead to the creation of micro-annulus or channel; and
 (b) the creation of defaults in the cement sheath.

The creation of micro-annulus can lead to fluid communication between drilled geological formations or fluid communication to annuli, contamination of groundwater and the pathway of fluids (oil, gas and/or water) to mud line or surface, which in catastrophic cases can injure personnel and cause complete destruction of the drilling rig or production platform.

The creation of defaults can generate water/gas ingress that may corrode the casing.

The response of the cement sheath due to mechanical or thermal loading may depend on its composition (chemical composition, water/cement ratio, additives), its hydration conditions (temperature, pressure, drained or undrained conditions, etc.), age and also the loading history.

Therefore it is very important to determine when it is safe to perform casing pressure tests (i.e. to apply loadings inside the casing) without damaging the cement sheath.

SUMMARY OF THE INVENTION

The invention relates to a method for determining a time window in which a casing pressure test can be performed without damaging a cement sheath, the method comprises:
 determining the hydration degree of the cement at a given time for a considered pressure and temperature values in the well;
 comparing the determined hydration degree and a predetermined value in the interval of [12%;30%];
 if the determined hydration degree is below the predetermined value, determining that the casing pressure test can be done without damaging the cement.

By altering the mechanical properties of the cement, it should be understood to mean altering the long-term/final mechanical properties of the cement.

There is a plurality of methods to determine the hydration degree of a cement (experimental methods or simulation methods). These methods are mentioned below.

It has been observed experimentally that, as long as the hydration degree of the cement slurry is below 12%-30%, the long-term/final mechanical properties of the cement are not altered by the application of a mechanical loading. This state is reached at a time called "critical time for Creation of Residual Strain (CRS)".

Therefore, this method provides an accurate determination of the period of time during which casing pressure tests may be performed to assess casing integrity.

The temperature value and the pressure value may be the temperature and pressure that are experienced by cement at a given depth in the well.

It is also possible to add a further step where a pressure casing test is performed if the determination is positive (i.e. it is determined that the pressure casing test may be performed).

In addition, the determination of the hydration degree may comprise a monitoring of heat flow of a cement slurry sample, said sample having a composition similar to a composition of the cement slurry, the sample being placed during the monitoring at a temperature equal to the temperature value and a pressure equal to the pressure value.

In a possible embodiment, the determination of the hydration degree may comprise a monitoring velocity of ultrasonic waves through a cement sample, said sample having a composition similar to a composition of the cement, the sample being placed during the monitoring at a temperature equal to the temperature value and a pressure that could be equal to the pressure value.

Said determination may be performed thanks to an UCA (ultrasonic cement analyzer).

In a possible embodiment, the determination of the hydration degree may comprise a monitoring of mechanical responses of a cement sample during loading cycles, said cement sample having a composition similar to a composition of the cement, the cement sample being placed during the monitoring at a temperature equal to the temperature value and a pressure that could be equal to the pressure value.

Said determination may be performed thanks to the STCA (Slurry To Cement Analyzer, US 2013/0192382 A1) or any other oedometric device.

The predetermined value may be in the interval of [18%-20%].

The determination of the critical time of CRS from UCA experiments is done as follows:
- emitting waves in a cement sample,
- monitoring, during a period of time, the velocity of the waves in the cement sample;
- determining a first time after starting the hydration of a cement sample corresponding to:
  - a maximum in the time derivative of the evolution of velocity during said period;
  - or an inflexion point in the evolution of velocity during said period;
- if a second time after starting the hydration of a cement in the well is below a third time below the determined first time, determining that the casing pressure test is acceptable without damaging of the cement in the well.

The first time is often named "critical time". The third time is often defined as a safety time below the critical time and chosen by industrial firms to ensure that the critical time is not reached.

As a matter of fact, this method is an alternative method for the method for determining a time window in which a casing pressure test can be performed without damaging a cement sheath mentioned above. No hydration degree is determined in said method but the physical concept are identical: the maximum in the time derivative or the inflexion point corresponds in fact to a hydration degree in the range of 12%-30% or in 18%-20%.

The emitted waves may be ultra-sonic waves.

The monitored waves may be compressive waves.

The emission and the monitoring of the waves/waves velocity may be performed in an UCA (ultrasonic cement analyzer).

It is also possible to add a further step where a pressure casing test is performed if the determination is positive (i.e. it is determined that the pressure casing test may be performed).

Another aspect relates to a computer program product comprising a computer-readable medium, having thereon a computer program comprising program instructions. The computer program is loadable into a data-processing unit and adapted to cause the data-processing unit to carry out the method described above when the computer program is run by the data-processing unit.

Other features and advantages of the method and apparatus disclosed herein will become apparent from the following description of non-limiting embodiments, with reference to the appended drawings.

BRIEF DESCRIPTION OF THE DRAWINGS

The present invention is illustrated by way of examples, and not by way of limitations, in the figures of the accompanying drawings, in which like reference numerals refer to similar elements and in which.

DETAILED DESCRIPTION OF THE DRAWINGS

To measure the degree of hydration of the cement, it is possible to use a number of methods such as:
- a method using an UCA (ultrasonic cement analyzer) (see for instance, «Effets des contraintes et de la température sur l'intégrité des ciments des puits pétroliers», Manh Huyen VU, 23 février 2012);
- a method based on calorimetric tests (see for instance, «Effets des contraintes et de la température sur l'intégrité des ciments des puits pétroliers», Manh Huyen VU, 23 février 2012);
- a method based on a mathematical model of the cement slurry;

For instance, during calorimetric tests, the heat flow generated due to hydration reaction is measured.

The degree of hydration $\xi(t)$ at a time t represents the ratio between the amount of heat $Q(t)$ released up to this time t and the total amount of heat generated by the cement for a complete hydration $Q_{TCP}$.

$$\xi(t) = \frac{Q(t)}{Q_{TCP}}$$

In addition, the weight fractions of cement powder constituents X are noted $m_X$.

In the cement slurry, the mass fraction of the cement powder is noted $m_C$ (the cement composition is mostly formed by $C_3S$, $C_2S$, $C_3A$ and $C_4AF$ and water—A special chemical notation established by cement chemist is adopted as a simple method for describing compounds. Abbreviations are given for the oxides most frequently encountered, such as C for CaO, S for SiO2, A for Al2O3 and F for Fe2O3. Thus Ca3SiO5 becomes C3S).

Knowing the total heat flow required to complete hydration of each component of the cement powder ($Q_T^X$), it is possible to compute $Q_T$ (total heat released for a complete hydration per mass unit of cement powder) and $Q_{TCP}$ (total heat released for a complete hydration per mass unit of the cement).

$$Q_T = \sum_X m_X Q_T^X$$

$$Q_{TCP} = \sum_X m_X m_C Q_T^X$$

Determination of the hydration degree of the cement may be performed in the laboratory by reproducing the condition of temperature, pressure, etc. of the wells but it takes hours to experiment.

Based on the above equations, it is possible to write that:

$$\frac{d\xi(t)}{dt} = \frac{1}{Q_{TCP}} \frac{dQ(t)}{dt}$$

It is noted that, if for a given pressure ($P_0$) and temperature ($T_0$) a predetermined value of the hydration $\xi$ is reached at a time $t_{crit0}$, it is possible to determine a time $t_{crit}$ when said predetermined value of the hydration $\xi$ is also reached but for different pressure (P) and temperature (T):

$$t_{crit}(T, P) = t_{crit0} \cdot e^{\frac{\Delta E}{R}\left(\frac{1}{T}-\frac{1}{T_0}\right)+\frac{\Delta V}{R}\left(\frac{P}{T}-\frac{P_0}{T_0}\right)}$$

Figure 1:
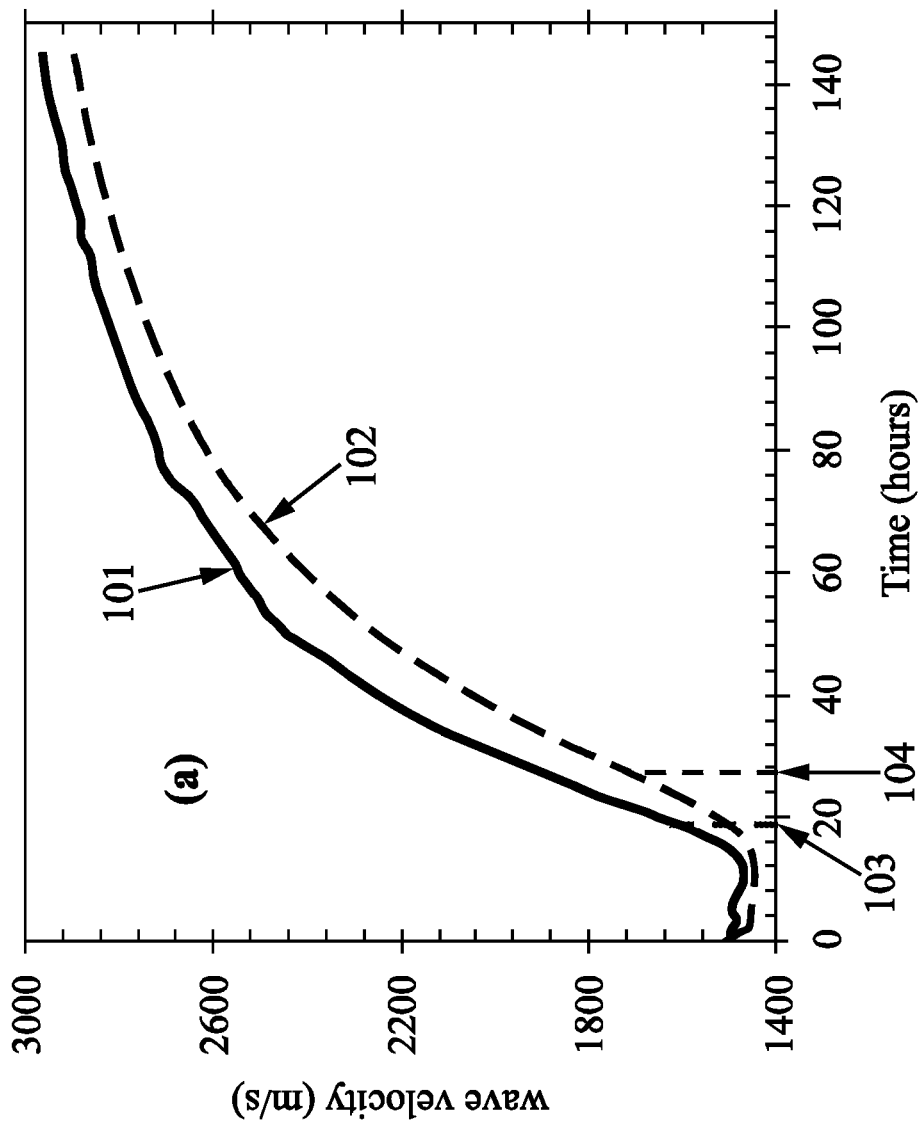
FIG. 1 is graph representing experimental monitoring of ultrasonic waves velocity in a cement sample.
Figure 2:
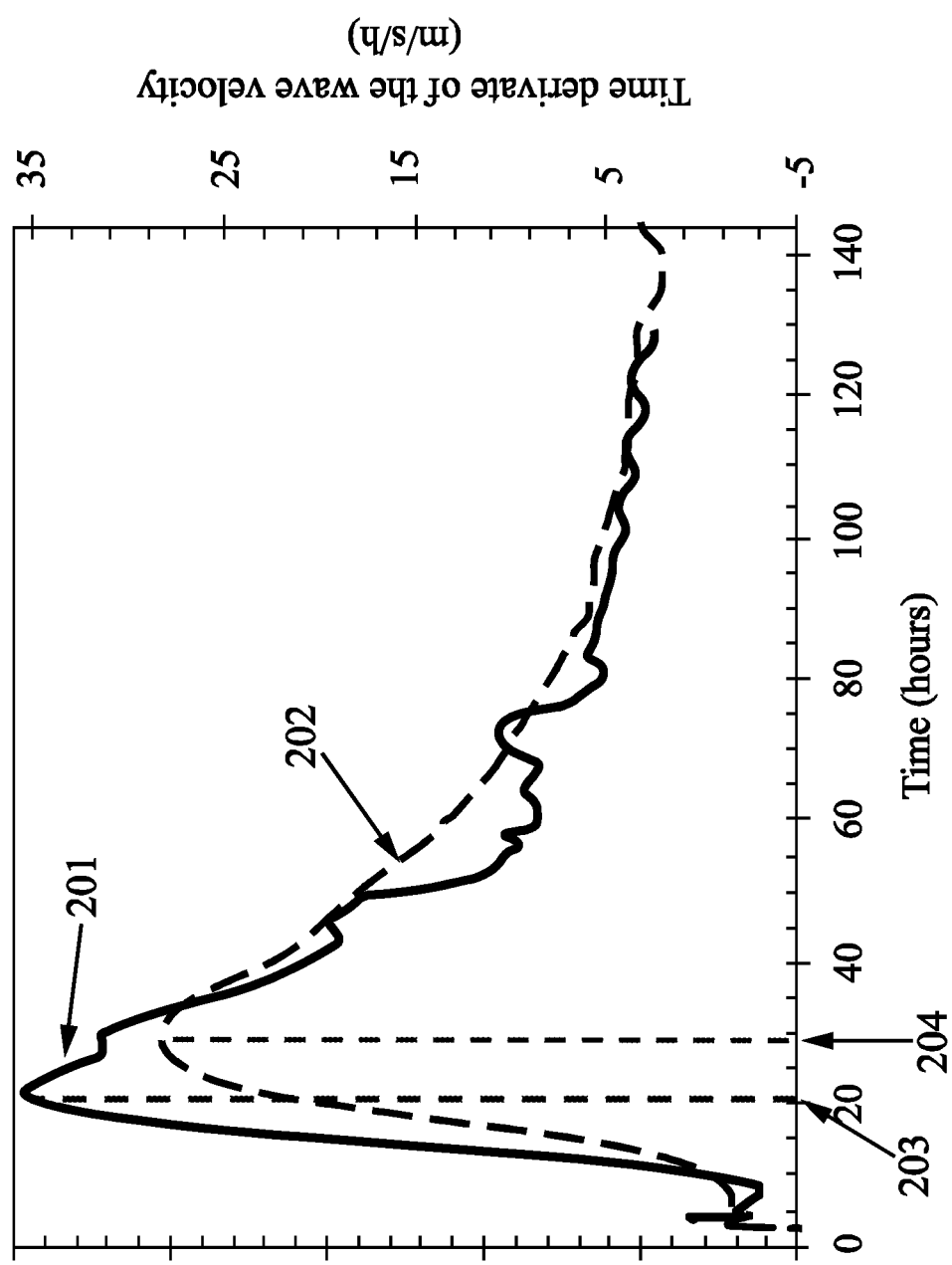
FIG. 2 is graph representing derivative of experimental results obtained from FIG. 1

With $\Delta E$ an molar energy activation parameter (e.g. 33800 J/mol+/−10%), $\Delta V$ a molar volume activation parameter (e.g. −34.4 cm$^3$/mol+/−10%), R the perfect gas constant FIGS. 1 and 2 are graphs representing experimental monitoring of ultrasonic waves in a cement sample.

The Ultrasonic Cement Analyzer (UCA) is one of the most used equipment in the petroleum industry, which permits to investigate the development of compressive strength of cement paste during its hydration by continuous measurement of the compression-wave velocity.

Two UCA tests are here performed: at 7° C., under 0.3 MPa and 25 MPa. The evolutions of the wave velocity with time are presented in FIG. 1:
  the curve 101 corresponds to the wave velocity of the ultrasonic compression-wave at 7° C. and 25 MPa;
  the curve 102 corresponds to the wave velocity of the ultrasonic compression-wave at 7° C. and 0.3 MPa.

It is noted that point 103 (respectively 104) corresponds to an inflection point of the curve 101 (respectively 102).

The derivative of wave velocity versus time is presented in FIG. 2.
  the curve 201 corresponds to the derivative of the wave velocity of the ultrasonic compression-wave at 7° C. and 25 MPa;
  the curve 202 corresponds to the derivative of the wave velocity of the ultrasonic compression-wave at 7° C. and 0.3 MPa.

It is noted that point 203 (respectively 204) corresponds to the maximum of the curve 201 (respectively 202).

The comparison of UCA experiments with the values of hydration degree shows that, points 103, 104, 203, and 204 may correspond to a hydration degree about 18-20% of the cement.

Therefore monitoring ultrasonic waves in the UCA enables the quick, simple and cheap determination of the critical time corresponding to the hydration degree of 18%-20%.

Figure 3:
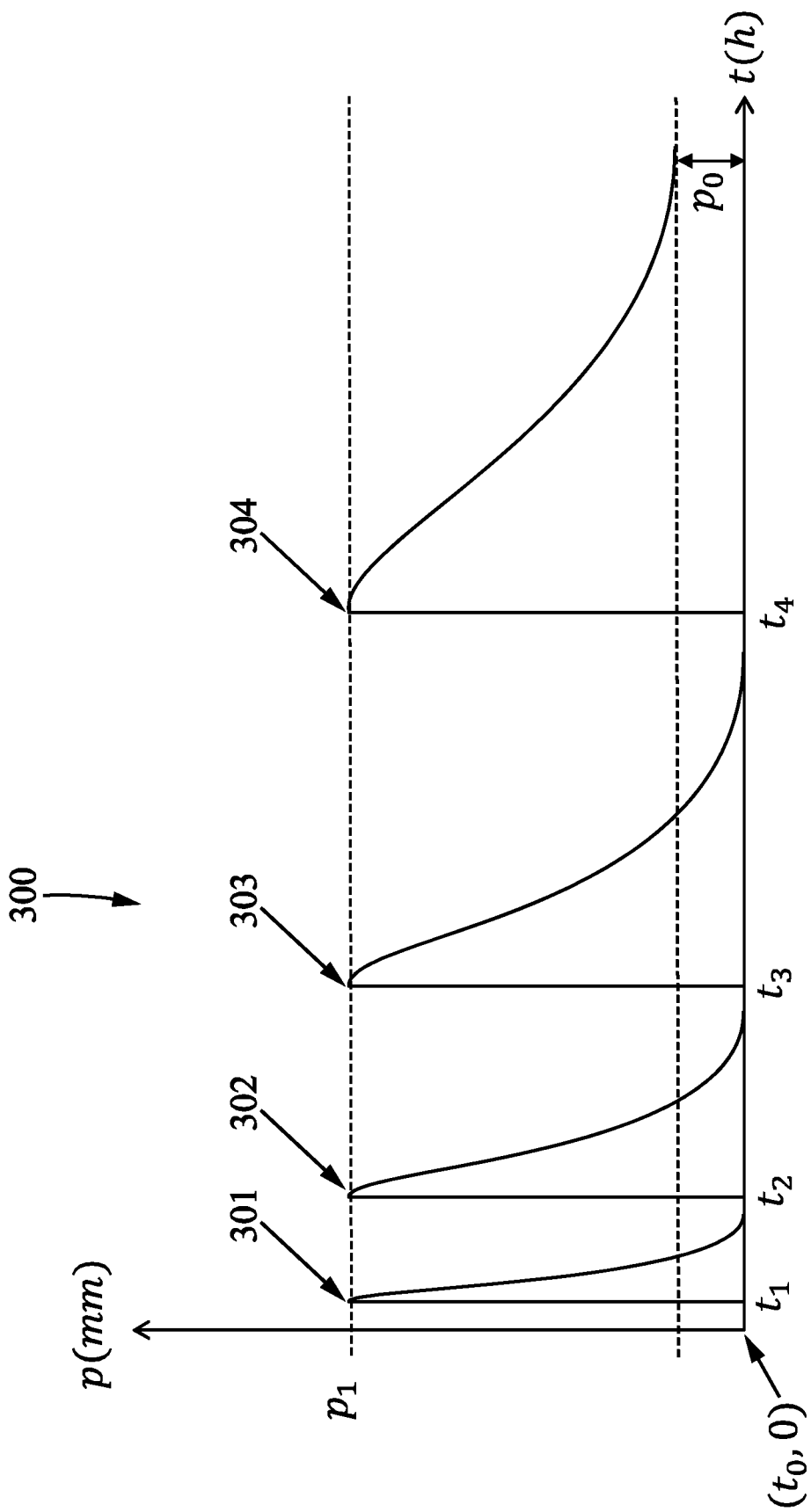
FIG. 3 is an example to understand the principle of determining a critical time after which no pressure casing test may be done.

FIG. 3 is an example to understand the principles of determining a critical time after which no pressure casing test may be done. It is noted that this example is performed at atmospheric pressure and normal temperature (e.g. 20° C.).

In this example, scars may be performed with a cutter on freshly mixed cement slurry so that the scars are similar to trenches with a depth of $p_1$ (e.g. 2 mm). The resorption of the scars/the diminution of the depth of the trenches are monitored.

The graph 300 of FIG. 3 illustrates this monitoring:
  at the time $t_1$, a trench of depth $p_1$ is created and it completely disappears before the time $t_2$ (see spike 301).
  at the time $t_2$, a trench of depth $p_1$ is created and it completely disappears before the time $t_3$ (see spike 302).
  at the time $t_3$, a trench of depth $p_1$ is created and it completely disappears before the time $t_4$ (see spike 303).
  at the time $t_4$, a trench of depth $p_1$ is created but the trench is not completely resorbed (see spike 304): the depth of the trench is never lesser than $p_0$>0.

Therefore, if the period of time during which the casing pressure test may be performed without damaging the cement (and affecting the final mechanical characteristics of the cement) is noted [$t_0$; $t_{crit}$], we may determine that $t_3 < t_{crit} < t_4$ in the previous experience associated with graph 300.

Therefore, by realizing a plurality of experiments with various time $t_1$, $t_2$, $t_3$, $t_4$, etc. we may determine a pretty accurate approximation of $t_{crit}$ the time before which the casing pressure test may be performed without damaging the cement.

As a matter of fact, it has been determined that $t_{crit}$ may be function of the setting conditions (i.e. temperature, pressure, water/cement ratio, additives, etc.).

Nevertheless, even if $t_{crit}$ may depend on a plurality of parameters, it has also been determined that the hydration degree of the cement slurry for a time corresponding to $t_{crit}$ is quite constant: the hydration degree corresponding to the experimental time $t_{crit}$ is about 18%-20% for all $t_{crit}$.

Therefore, casings pressure tests may be performed without damaging the cement as long as the hydration degree of the cement slurry is below 18%-20%. In order to deal with a margin of safety, it may be considered in oil and gas industry that casings pressure tests may be performed without damaging the cement as long as the hydration degree of the cement slurry is below 12%-18%.

It is noted that an accurate experiment to determine the critical time $t_{crit}$ in various conditions of pressure and temperature may be performed thanks to a STCA (Slurry To Cement Analyzer, US 2013/0192382 A1): a plurality of cycles of constraints may thus be applied as described in § 4.3 and § 4.4 of the Thesis of Nicolaine AGOFACK, 2015, *Comportement des ciments pétroliers aujeune âge et integrite des puits* or of the application EP15305279 in order to assess the plasticity response of the cement (see FIG. 4-16 of said documents). Similar results may be found.

Figure 4:
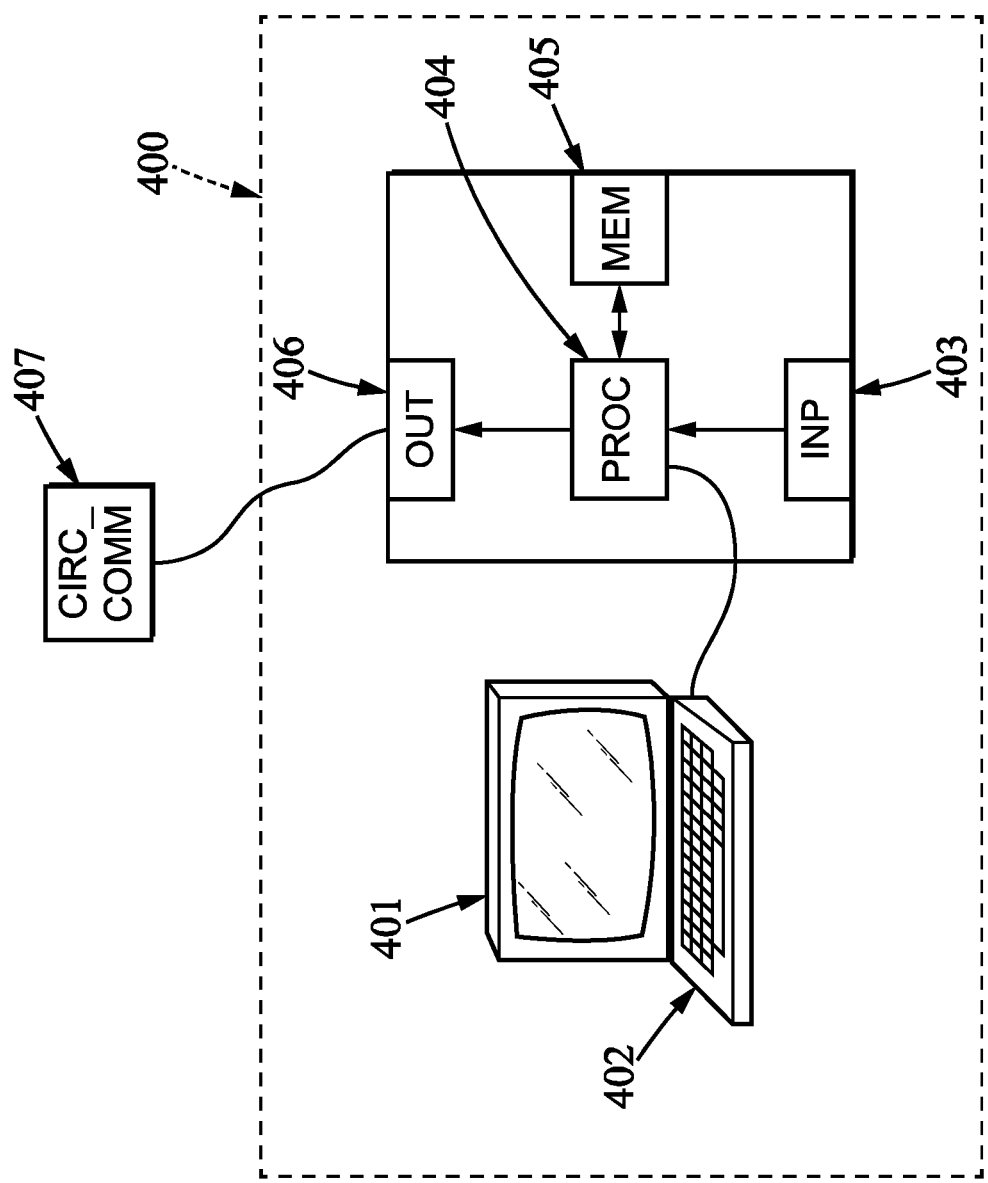
FIG. 4 is a possible embodiment for a device that enables the present invention.

FIG. 4 is a possible embodiment for a device that enables the present invention.

In this embodiment, the device 400 comprise a computer, this computer comprising a memory 405 to store program instructions loadable into a circuit and adapted to cause circuit 404 to carry out the steps of the present invention when the program instructions are run by the circuit 404.

The memory 405 may also store data and useful information for carrying the steps of the present invention as described above.

The circuit 404 may be for instance:
  a processor or a processing unit adapted to interpret instructions in a computer language, the processor or the processing unit may comprise, may be associated with or be attached to a memory comprising the instructions, or
  the association of a processor/processing unit and a memory, the processor or the processing unit adapted to interpret instructions in a computer language, the memory comprising said instructions, or an electronic card wherein the steps of the invention are described within silicon, or a programmable electronic chip such as a FPGA chip (for "Field-Programmable Gate Array").

This computer comprises an input interface 403 for the reception of data used for the above method according to the invention and an output interface 406 for providing the time period during which casings tests may be performed without damaging the cement.

To ease the interaction with the computer, a screen 401 and a keyboard 402 may be provided and connected to the computer circuit 404.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

A person skilled in the art will readily appreciate that various parameters disclosed in the description may be modified and that various embodiments disclosed may be combined without departing from the scope of the invention.

The invention claimed is:

1. A method for determining a time window in which a casing pressure test can be performed without damaging a cement sheath, the method comprises:

determining a hydration degree of the cement at a given time for a considered pressure and temperature values in a well;

comparing the determined hydration degree and a predetermined value in an interval of 12%-30%;

if the determined hydration degree is below the predetermined value, determining that the casing pressure test can be done without damaging the cement sheath.

2. The method according to claim 1, wherein the determination of the hydration degree comprises a monitoring of a heat flow of a cement sample, said cement sample having a composition similar to a composition of the cement, the cement sample being placed during the monitoring at a temperature equal to the temperature value and a pressure equal to the pressure value.

3. The method according to claim 1, wherein the determination of the hydration degree comprises a monitoring of ultrasonic waves of a cement sample, said cement sample having a composition similar to a composition of the cement, the cement sample being placed during the monitoring at a temperature equal to the temperature value and a pressure that could be equal to the pressure value.

4. The method according to claim 1, wherein the determination of the hydration degree comprises a monitoring of a mechanical response of a cement sample during cycles of constraints, said cement sample having a composition similar to a composition of the cement, the cement sample being placed during the monitoring at a temperature equal to the temperature value and a pressure that could be equal to the pressure value.

5. The method according to claim 1, wherein the predetermined value is in an interval of 18%-20%.

6. A method for determining a time window in which a casing pressure test can be performed without damaging a cement sheath, the method comprises:

emitting waves in a cement sample, monitoring, during a period of time, an evolution of the velocity of the waves in the cement sample;

determining a first time after starting the hydration of a cement sample corresponding to:

a maximum in the time derivative of the evolution of velocity during said period;

or an inflexion point in the evolution of velocity during said period;

if a second time after starting the hydration of a cement in the well is below a third time below the determined first time, determining that the casing pressure test is acceptable without damaging the cement sheath in a well.

7. A non-transitory computer readable storage medium, having stored thereon a computer program comprising program instructions, the computer program being loadable into a data-processing unit and adapted to cause the data-processing unit to carry out the steps of claim 1 when the computer program is run by the data-processing device.

* * * * *